(12) United States Patent
Speth et al.

(10) Patent No.: US 12,343,177 B2
(45) Date of Patent: Jul. 1, 2025

(54) VIDEO BASED DETECTION OF PULSE WAVEFORM

(71) Applicants: Securiport LLC, Washington, DC (US); Department of Computer Science and Engineering University of Notre Dame, Notre Dame, IN (US)

(72) Inventors: Jeremy Speth, South Bend, IN (US); Patrick Flynn, South Bend, IN (US); Adam Czajka, South Bend, IN (US); Kevin Bowyer, South Bend, IN (US); Nathan Carpenter, Washington, DC (US); Leandro Olie, Washington, DC (US)

(73) Assignees: Securiport LLC, Reston, VA (US); University of Notre Dame du Lac, South Bend, IN (US)

( * ) Notice: Subject to any disclaimer, the term of this patent is extended or adjusted under 35 U.S.C. 154(b) by 587 days.

(21) Appl. No.: 17/591,929

(22) Filed: Feb. 3, 2022

(65) Prior Publication Data

US 2022/0240865 A1     Aug. 4, 2022

Related U.S. Application Data

(60) Provisional application No. 63/145,140, filed on Feb. 3, 2021.

(51) Int. Cl.
*A61B 5/00*     (2006.01)
*A61B 5/024*     (2006.01)
(Continued)

(52) U.S. Cl.
CPC ........ *A61B 5/7278* (2013.01); *A61B 5/02405* (2013.01); *A61B 5/1128* (2013.01);
(Continued)

(58) Field of Classification Search
CPC . A61B 5/02416; A61B 5/0077; A61B 5/7278; G06T 2207/30076; G06T 7/0012; G06V 40/15
See application file for complete search history.

(56) References Cited

U.S. PATENT DOCUMENTS

2013/0296660 A1    11/2013    Tsien et al.
2015/0223700 A1*    8/2015    Kirenko ............. A61B 5/14551
                                                                                               600/476
(Continued)

FOREIGN PATENT DOCUMENTS

EP          3127485 B1    10/2019
WO    2020247894 A1    12/2020

OTHER PUBLICATIONS

De Haan, Gerard, and Vincent Jeanne. "Robust pulse rate from chrominance-based rPPG." IEEE transactions on biomedical engineering 60.10 (2013): 2878-2886. (Year: 2013).*

(Continued)

*Primary Examiner* — Raphael Schwartz
(74) *Attorney, Agent, or Firm* — MILES & STOCKBRIDGE P.C.

(57) ABSTRACT

The video based detection of pulse waveform includes systems, devices, methods, and computer-readable instructions for capturing a video stream including a sequence of frames, processing each frame of the video stream to spatially locate a region of interest, cropping each frame of the video stream to encapsulate the region of interest, processing the sequence of frames, by a 3-dimensional convolutional neural network, to determine the spatial and temporal dimensions of each frame of the sequence of frames and to produce a pulse waveform point for each frame of the sequence of frames, and generating a time series of pulse (Continued)

waveform points to generate the pulse waveform of the subject for the sequence of frames.

21 Claims, 4 Drawing Sheets

(51) Int. Cl.
  *A61B 5/11* (2006.01)
  *G06F 17/14* (2006.01)
  *G06V 10/25* (2022.01)
  *G06V 10/80* (2022.01)
  *G06V 10/82* (2022.01)
  *G06V 20/40* (2022.01)
  *G06V 40/16* (2022.01)

(52) U.S. Cl.
  CPC .......... *A61B 5/7235* (2013.01); *G06F 17/141* (2013.01); *G06V 10/25* (2022.01); *G06V 10/80* (2022.01); *G06V 10/82* (2022.01); *G06V 20/46* (2022.01); *G06V 40/161* (2022.01)

(56) References Cited

U.S. PATENT DOCUMENTS

2018/0270436 A1  9/2018  Ivarsson et al.
2020/0121256 A1* 4/2020  McDuff ............... A61B 5/0077
2020/0337776 A1  10/2020 Saun et al.

OTHER PUBLICATIONS

Yu, Zitong, Xiaobai Li, and Guoying Zhao. "Remote photoplethysmograph signal measurement from facial videos using spatio-temporal networks." arXiv preprint arXiv:1905.02419 (2019). (Year: 2019).*
International Search Report & Written Opinion of the ISR for corresponding PCT Application No. PCT/IB2022/050960 mailed May 11, 2022.
Gerald de Haan et al., "Robust Pulse Rate From Chrominance-Based rPPG", IEEE Transactions on Biomedical Engineering, vol. 60, No. 10, pp. 2878-2886, Oct. 2013.
Ming-Zher Poh et al., "Non-contact, automated cardiac pulse measurements using video imaging and blind source separation.", Optics Express, vol. 18, No. 10, pp. 10762-10774, May 10, 2010.
Ming-Zher Poh et al., "Advancements in Noncontact, Multiparameter Physiological Measurements Using a Webcam", IEEE Transactions on Biomedical Engineering, vol. 58, No. 1, pp. 7-11, Jan. 2011.
W. Wang et al., Algorithmic principles of remote-PPG, IEEE Transactions on Biomedical Engineering, 64(7), pp. 1479-1491, DOI: 10.1109/TBME.2016.2609282, Jan. 7, 2017.
Zitong Yu et al., "Remote Photoplethysmograph Signal Measurement from Facial Videos Using Spatio-Temporal Networks", RPPG Measurement Using Spatio-Temporal Networks, pp. 1-12, 2019.

* cited by examiner

VIDEO BASED DETECTION OF PULSE WAVEFORM

PRIORITY INFORMATION

This application claims the benefits of U.S. Provisional Patent Application No. 63/145,140, filed on Feb. 3, 2021, which is incorporated herein by reference in its entirety.

BACKGROUND OF THE INVENTION

Field of the Invention

The embodiments of the present invention generally relate to use of biometrics, and more particularly, to video based detection of pulse waveform and/or heart rate for a subject.

Discussion of the Related Art

In general, biometrics may be used to track vital signs that provide indicators about a subject's physical state that may be used in a variety of ways. As an example, for border security or health monitoring, vital signs may be used to screen for health risks (e.g., temperature). While sensing temperature is a well-developed technology, collecting other useful and accurate vital signs such as pulse rate (i.e., heart rate or heart beats per minute) or pulse waveform has required physical devices to be attached to the subject. The desire to perform this measurement without physical contact has produced some video based techniques, however, these are generally limited in accuracy, require control of the subject's posture, and/or require a close positioning of the camera.

Performing reliable pulse rate or pulse waveform estimation from a camera sensor is more difficult than contact plethysmography for several reasons. The change in reflected light from the skin's surface, because of light absorption of blood, is very minor compared to those caused by changes in illumination. Even in settings with ambient lighting, the subject's movements drastically change the reflected light and overpower the pulse signal.

Existing approaches to remote pulse estimation operate on the spatial and temporal dimensions separately. Typically, the spatial region of interest containing skin is converted to a single or few values for each frame independently, followed by processing over the temporal dimension to produce a pulse waveform. While this is effective for stationary subjects, it presents difficulties when the subject moves (e.g., talks). Examples of independent analysis of the spatial and temporal dimensions include independent component analysis (Poh 2010, Poh 2011), chrominance analysis (De Haan 2013), and plane orthogonal to skin (Wang 2017).

Accordingly, the inventors have developed systems, devices, methods, and computer-readable instructions that enable accurate capture of a pulse waveform without physical contact and with minimal constraints on the subject's movement and position.

SUMMARY OF THE INVENTION

Accordingly, the present invention is directed to a video based detection of pulse waveform that substantially obviates one or more problems due to limitations and disadvantages of the related art.

Objects of the present invention provide systems, devices, methods, and computer-readable instructions that enable accurate capture of a pulse waveform without physical contact and with minimal constraints on the subject's movement and position.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described, the video based detection of pulse waveform includes systems, devices, methods, and computer-readable instructions for capturing a video stream including a sequence of frames, processing each frame of the video stream to spatially locate a region of interest, cropping each frame of the video stream to encapsulate the region of interest, processing the sequence of frames, by a 3-dimensional convolutional neural network, to determine the spatial and temporal dimensions of each frame of the sequence of frames and to produce a pulse waveform point for each frame of the sequence of frames, and generating a time series of pulse waveform points to generate the pulse waveform of the subject for the sequence of frames.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

DETAILED DESCRIPTION OF THE INVENTION

Figure 1:
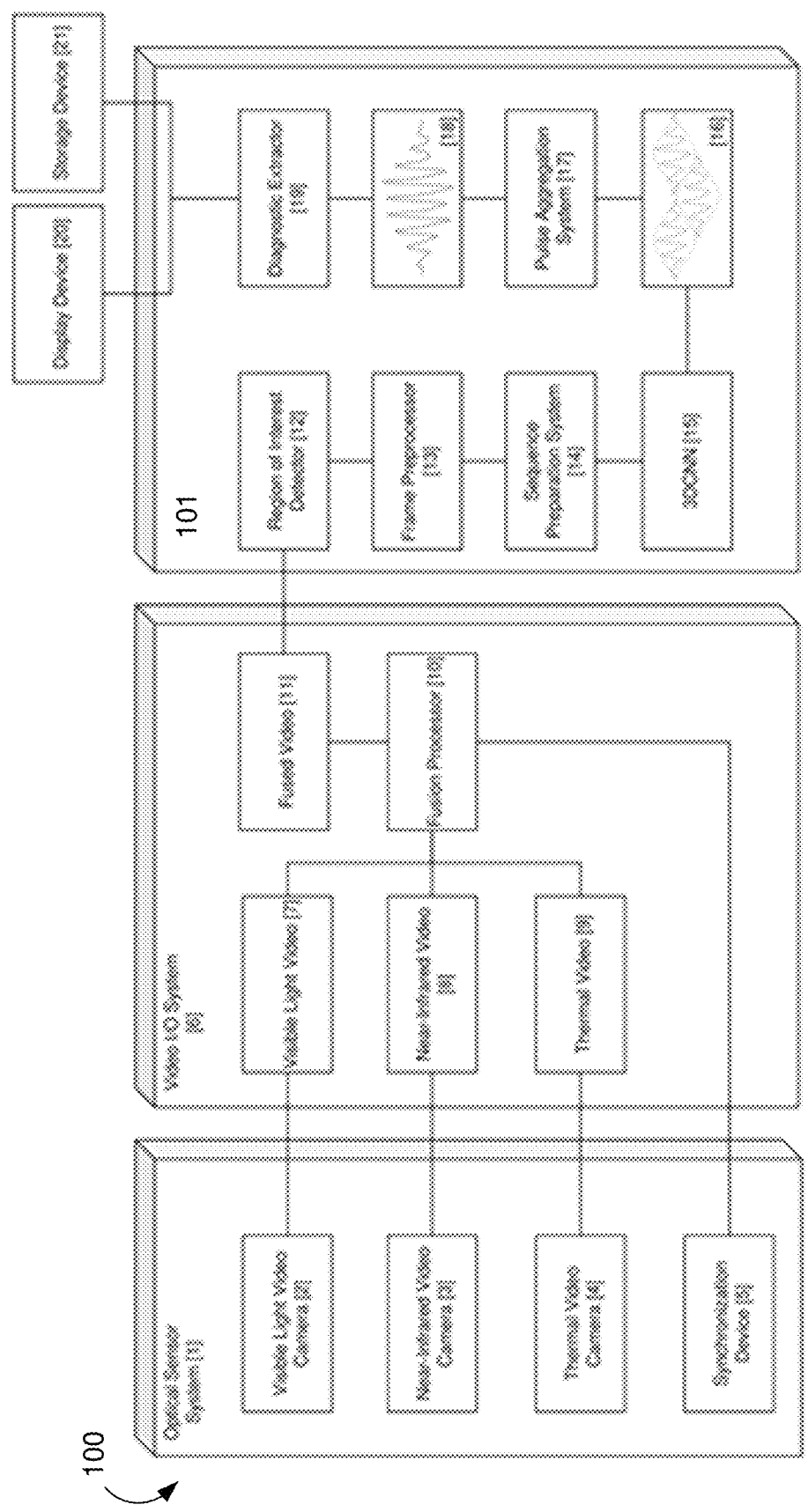
FIG. 1 illustrates a system for pulse waveform estimation according to an example embodiment of the present invention.

Reference will now be made in detail to the embodiments of the present invention, examples of which are illustrated in the accompanying drawings. Wherever possible, like reference numbers will be used for like elements.

Embodiments of user interfaces and associated methods for using a device are described. It should be understood, however, that the user interfaces and associated methods can be applied to numerous devices types, such as a portable communication device such as a tablet or mobile phone. The portable communication device can support a variety of applications, such as wired or wireless communications. The various applications that can be executed on the device can use at least one common physical user-interface device, such as a touchscreen. One or more functions of the touchscreen as well as corresponding information displayed on the device can be adjusted and/or varied from one application to another and/or within a respective application. In this way, a common physical architecture of the device can support a variety of applications with user interfaces that are intuitive and transparent.

The embodiments of the present invention provide systems, devices, methods, and computer-readable instructions to measure one or more biometrics, including heart-rate and pulse waveform, without physical contact with the subject. In the various embodiments, the systems, devices, methods, and instructions collect, process, and analyze video taken in one or more modalities (e.g., visible light, near infrared, thermal, etc.) to produce an accurate pulse waveform for the subject's heartbeat from a distance without constraining the subject's movement or posture. The pulse waveform for the subject's heartbeat may be used as a biometric input to establish features of the physical state of the subject and how they change over a period of observation (e.g., during questioning or other activity).

Remote photoplethysmography (rPPG) is the monitoring of blood volume pulse from a camera at a distance. Using rPPG, blood volume pulse from video at a distance from the skin's surface may be detected. The embodiments of the invention provide an estimate of the blood volume to generate a pulse waveform from a video of one or more subjects at a distance from a camera sensor. Additional diagnostics can be extracted from the pulse waveform such as heart rate (beats per minute) and heart rate variability to further assess the physiological state of the subject. The heart rate is a concise description of the dominant frequency in the blood volume pulse, represented in beats per minute (bpm), where one beat is equivalent to one cycle.

The embodiments of the present invention (concurrently, simultaneously, in-parallel, etc.) process the spatial and the temporal dimensions of video stream data using a 3-dimensional convolutional neural network (3DCNN). The main advantage of using 3-dimensional kernels within the 3DCNN is the empirical robustness to movement, talking, and a general lack of constraints on the subject. Additionally, the embodiments provide concise techniques in which the 3DCNN is given a sequence of images and produces a discrete waveform with a real value for every frame. While an existing work has deployed a 3DCNN for pulse detection (Yu 2019), the embodiments of the present invention significantly improve the model by modifying the temporal dimension of the 3D kernels with dilations as a function of their depth within the 3DCNN. As a result, a significant improvement in heart rate estimation without increasing the model size or computational requirements is achieved.

Another advantage of the embodiments of the present invention over existing methods is the ability to estimate reliable pulse waveforms rather than relying on long-term descriptions of the signal. Many existing approaches use handcrafted features. By contrast, the embodiments utilize one or more large sets of data. Existing approaches were validated by comparing their estimated heart rate to the subject's physically measured heart rate, which is only a description of the frequency of a signal over long time intervals. By contrast, the embodiments were optimized and validated over short time intervals (e.g., video streams less than 10 seconds, video streams less than 5 seconds, video streams less than 3 seconds) to produce reliable estimates of the pulse waveform rather than a single frequency or heart-rate value, which enables further extraction of information to better understand the subject's physiological state.

FIG. 1 illustrates a system 100 for pulse waveform estimation according to an example embodiment of the present invention. System 100 includes optical sensor system 1, video I/O system 6, and video processing system 101.

Optical sensor system 1 includes one or more camera sensors, each respective camera sensor configured to capture a video stream including a sequence of frames. For example, optical sensor system 1 may include a visible-light camera 2, a near-infrared camera 3, a thermal camera 4, or any combination thereof. In the event that multiple camera sensors are utilized (e.g., single modality or multiple modality), the resulting multiple video streams may be synchronized according to synchronization device 5. Alternatively, or additionally, one or more video analysis techniques may be utilized to synchronize the video streams.

Video I/O system 6 receives the captured one or more video streams. For example, video I/O system 6 is configured to receive raw visible-light video stream 7, near-infrared video stream 8, and thermal video stream 9 from optical sensor system 1. Here, the received video streams may be stored according to known digital format(s). In the event that multiple video streams are received (e.g., single modality or multiple modality), fusion processor 10 is configured to combine the received video streams. For example, fusion processor 10 may combine visible-light video stream 7, near-infrared video stream 8, and/or thermal video stream 9 into a fused video stream 11. Here, the respective streams may be synchronized according to the output (e.g., a clock signal) from synchronization device 5.

At video processing system 101, region of interest detector 12 detects (i.e., spatially locate) one or more spatial regions of interest (ROI) within each video frame. The ROI may be a face, another body part (e.g., a hand, an arm, a foot, a neck, etc.) or any combination of body parts. Initially, region of interest detector 12 determines one or more coarse spatial ROIs within each video frame. Region of interest detector 12 is robust to strong facial occlusions from face masks and other head garments. Subsequently, frame pre-processor 13 crops the frame to encapsulate the one or more ROI. In some embodiments, the cropping includes each frame being downsized by bi-cubic interpolation to reduce the number of image pixels to be processed. Alternatively, or additionally, the cropped frame may be further resized to a smaller image.

Sequence preparation system 14 aggregates batches of ordered sequences or subsequences of frames from frame processer 13 to be processed. Next, 3-Dimensional Convolutional Neural Network (3DCNN) 15 receives the sequence or subsequence of frames from the sequence preparation system 14. 3DCNN 15 processes the sequence or subsequence of frames, by a 3-dimensional convolutional neural network, to determine the spatial and temporal dimensions of each frame of the sequence or subsequence of frames and to produce a pulse waveform point for each frame of the sequence of frames. 3DCNN 15 applies a series of 3-dimensional convolution, averaging, pooling, and nonlinearities to produce a 1-dimensional signal approximating the pulse waveform 16 for the input sequence or subsequences.

In some configurations, pulse aggregation system 17 combines any number of pulse waveforms 16 from the sequences or subsequences of frames into an aggregated pulse waveform 18 to represent the entire video stream. Diagnostic extractor 19 is configured to compute the heart rate and the heart rate variability from the aggregated pulse waveform 18. To identify heart rate variability, the calculated heart rate of various subsequences may be compared. Display unit 20 receives real-time or near real-time updates from diagnostic extractor 19 and displays aggregated pulse waveform 18, heart rate, and heart rate variability to an operator. Storage Unit 21 is configured to store aggregated pulse waveform 18, heart rate, and heart rate variability associated with the subject.

Additionally, or alternatively, the sequence of frames may be partitioned into a partially overlapping subsequences within the sequence preparation system 14, wherein a first subsequence of frames overlaps with a second subsequence of frames. The overlap in frames between subsequences prevents edge effects. Here, pulse aggregation system 17 may apply a Hann function to each subsequence, and the overlapping subsequences added to generate aggregated pulse waveform 18 with the same number of samples as frames in the original video stream. In some configurations, each subsequence is individually passed to the 3DCNN 15, which performs a series of operations to produce a pulse waveform for each subsequence 16. Each pulse waveform output from the 3DCNN 15 is a time series with a real value for each video frame. Since each subsequence is processed by the 3DCNN 15 individually, they are subsequently recombined.

In some embodiments, one or more filters may be applied to the region of interest. For example, one or more wavelengths of LED light may be filtered out. The LED may be shone across the entire region of interest and surrounding surfaces or portions thereof. Additionally, or alternatively, temporal signals in non-skin regions may be further processed. For example, analyzing the eyebrows or the eye's sclera may identify changes strongly correlated with motion, but not necessarily correlated with the photplethysmogram. If the same periodic signal predicted as the pulse is found on non-skin surfaces, it may indicate a non-real subject or attempted security breach.

Although illustrated as a single system, the functionality of system 100 may be implemented as a distributed system. Further, the functionality disclosed herein may be implemented on separate servers or devices that may be coupled together over a network, such as a security kiosk coupled to a backend server. Further, one or more components of system 100 may not be included. For example, system 100 may be a smartphone or tablet device that includes a processor, memory, and a display, but may not include one or more of the other components shown in FIG. 1. The embodiments may be implemented using a variety of processing and memory storage devices. For example, a CPU and/or GPU may be used in the processing system to decrease the runtime and calculate the pulse in near real-time. System 100 may be part of a larger system. Therefore, system 100 may include one or more additional functional modules.

Figure 2:
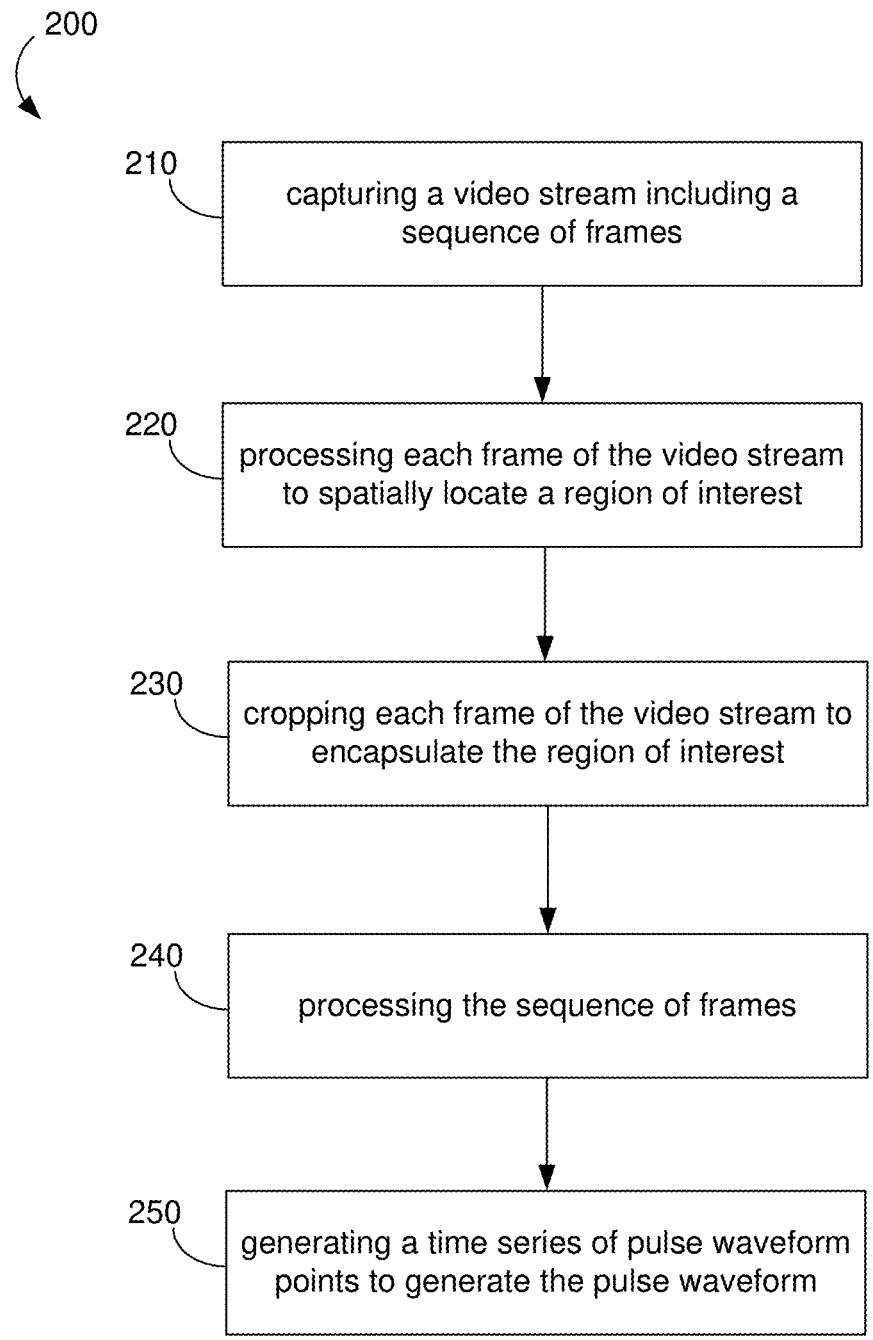
FIG. 2 illustrates a computer-implemented method for generating a pulse waveform according to an example embodiment of the present invention.

FIG. 2 illustrates a computer-implemented method 200 for generating a pulse waveform according to an example embodiment of the present invention.

At 210, a video stream including a sequence of frames is captured. The video stream may include one or more of a visible-light video stream, a near-infrared video stream, and a thermal video stream of a subject. In some instances, method 200 combines at least two of the visible-light video stream, the near-infrared video stream, and/or the thermal video stream into a fused video stream to be processed. The visible-light video stream, the near-infrared video stream, and/or the thermal video stream are combined according to a synchronization device and/or one or more video analysis techniques.

Next, at 220, each frame of the video stream is processed to spatially locate a region of interest. The ROI may be a face, another body part (e.g., a hand, an arm, a foot, a neck, etc.), or any combination of body parts.

Subsequently, at 230, each frame of the video stream is cropped to encapsulate the region of interest. For example, the cropping may include each frame being downsized by bi-cubic interpolation to reduce the number of image pixels to be processed.

At 240, the sequence of frames is processed, by a 3-dimensional convolutional neural network, to determine the spatial and temporal dimensions of each frame of the sequence of frames and to produce a pulse waveform point for each frame of the sequence of frames.

Lastly, at 250, a time series of pulse waveform points is generated to determine the pulse waveform of the subject for the sequence of frames. In some instances, the sequence of frames may be partitioned into a partially overlapping subsequences, wherein a first subsequence of frames overlaps with a second subsequence of frames. Here, a Hann function may be applied to each subsequence, and the overlapping subsequences added to generate the pulse waveform. In the various embodiments, the pulse waveform may be utilized to calculate a heart rate or heart rate variability. To identify heart rate variability, the calculated heart rate of various subsequences may be compared.

Figure 3:
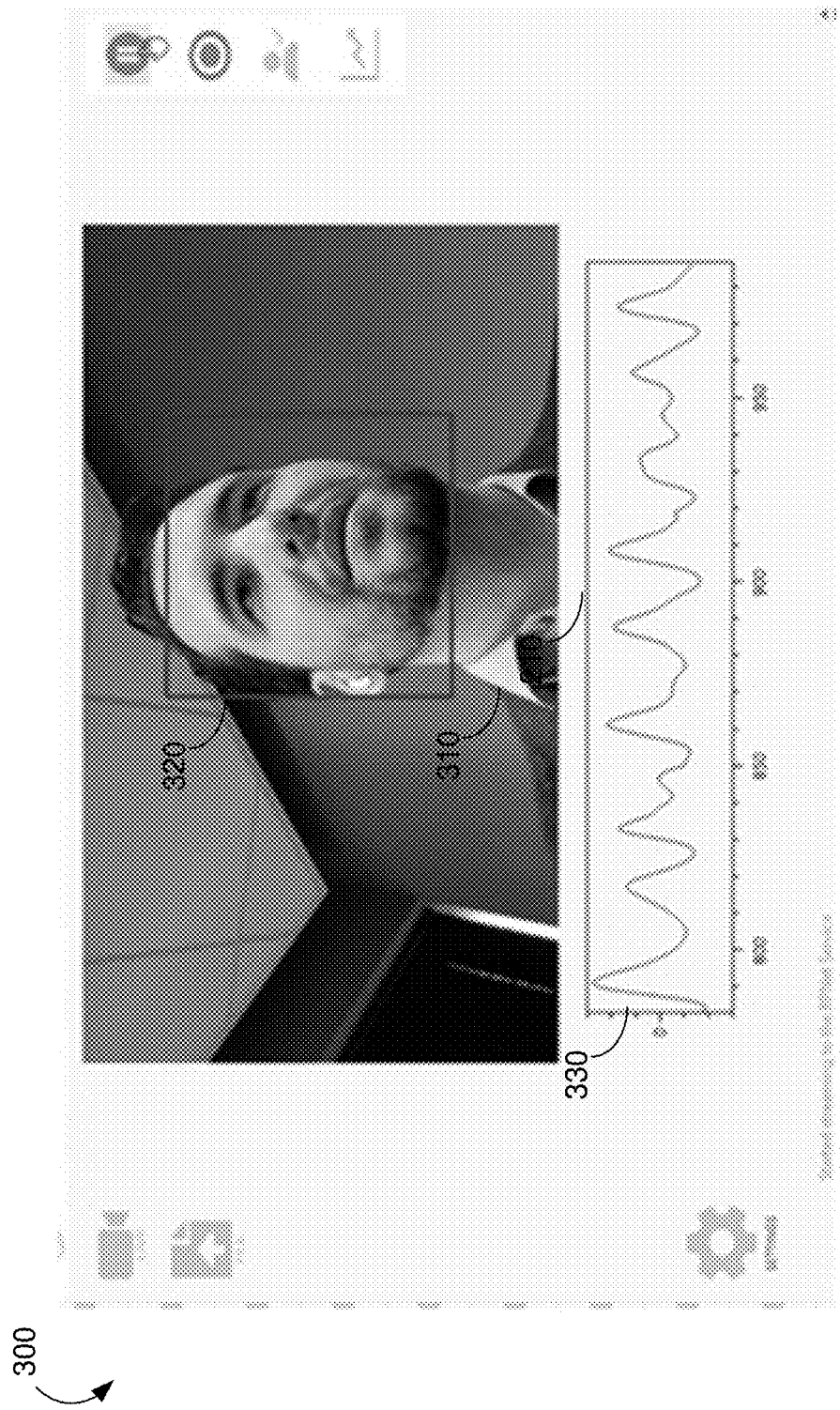
FIG. 3 illustrates a video based application for generating a pulse waveform according to an example embodiment of the present invention.

FIG. 3 illustrates a video based application 300 for generating a pulse waveform according to an example embodiment of the present invention. As illustrated in FIG. 3, application 300 displays the captured video stream of subject 310. Each frame of the captured video stream is processed to spatially locate a region of interest 320. For example, region of interest 320 may encapsulate one or more body parts of subject 310, such as the face. Using the various techniques described herein, the pulse waveform 330 of subject 310 is generated and displayed.

Figure 4:
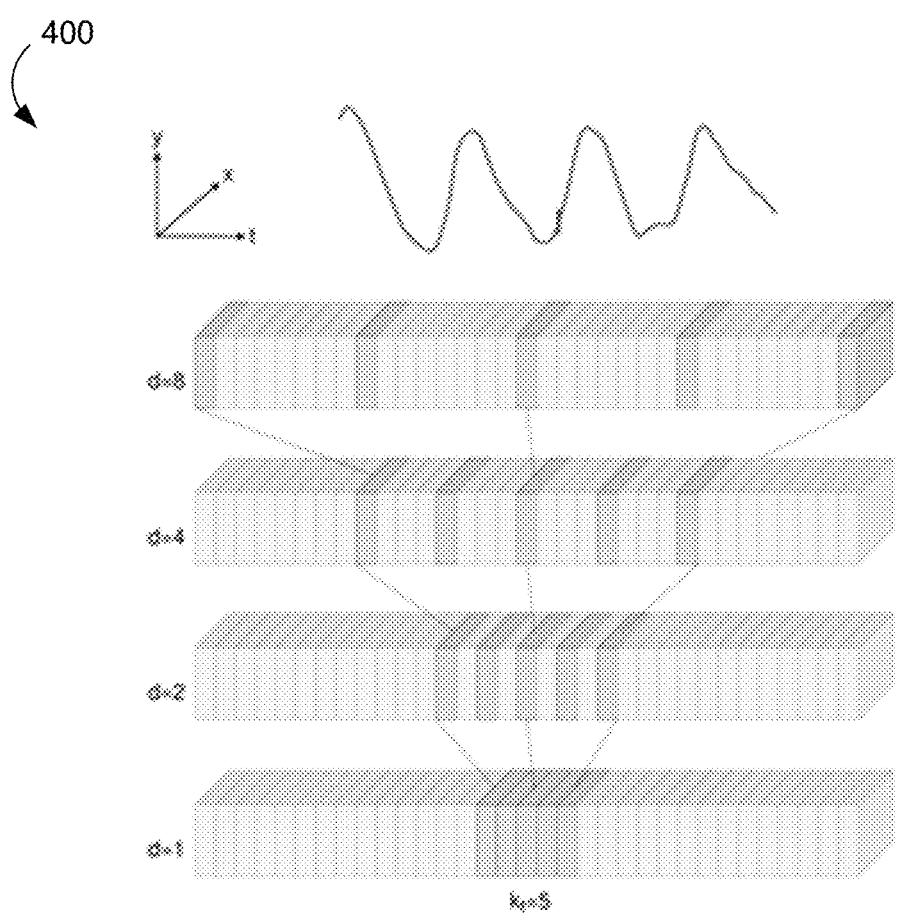
FIG. 4 illustrates an exponentially increasing dilation rate as a function of network depth.

FIG. 4 is a graphical representation 400 that illustrates an exponentially increasing dilation rate as a function of network depth. As illustrated, dilation rate is increased along the temporal axis of the 3D convolutions at depth d=1-4, giving increasing temporal receptive field while keeping kernel width constant at $k_t=5$. Here, the embodiments of the present invention significantly improve the model by modifying the temporal dimension of the three-dimensional (3D) kernels with dilations as a function of their depth within the 3DCNN. The embodiments of the present invention significantly improve the model by providing a wider temporal context of the pulse signal.

The embodiments of the present invention may be readily applied to numerous applications and domains. Numerous, but non-exhaustive, examples will be discussed. In some embodiments, the techniques described herein may be applied at an immigration kiosk, border control booth, entry gate, or the like. In other embodiments, the techniques described herein may be applied at an electronic device (e.g., tablet, mobile phone, computer, etc.) that hosts a video analysis application, such as a social media application or health monitoring application. In yet other embodiments, the techniques described herein may be used to distinguish between liveness and conversely synthetic video (e.g., deep fake video) by checking for expected differences in the pulse waveform detected at respective regions of interest (e.g., in the face and hand regions of interest).

The techniques described herein may be readily applied to numerous health monitoring/telemedicine and other applications and domains. Examples include injury precursor detection, impairment detection, health or biometric monitoring (e.g., vitals, stroke, concussion, cognitive testing, recovery tracking, diagnostics, alerts, physical therapy, cognitive test, physical symmetry, and biometric collection), stress detection (e.g., anxiety, nervousness, excitement), epidemic monitoring, illness detection, infant monitoring (e.g., sudden infant death syndrome (SIDS)), monitoring interest in an activity (e.g., video application, focus group testing, gaming applications), monitoring for non-verbal communication dues and deception (e.g., gambling applications), monitoring for non-verbal communication dues. In addition, the techniques described herein may be readily applied to exercise engagement as well as entertainment, audience, and other monitoring applications.

By implementing the various embodiments, the video stream time duration for extracting information is reduced, and additional information is determined by analyzing the video stream. The embodiments were optimized and validated over short time intervals to produce reliable estimates of the pulse waveform rather than a description of the blood volume's frequency of periodic changes in blood volume.

It will be apparent to those skilled in the art that various modifications and variations can be made in the video based detection of pulse waveform of the present invention without departing from the spirit or scope of the invention. Thus, it is intended that the present invention cover the modifications and variations of this invention provided they come within the scope of the appended claims and their equivalents.

What is claimed is:

1. A computer-implemented method for generating a pulse waveform, the computer-implemented method comprising:
    capturing a video stream including a sequence of frames;
    processing each frame of the video stream to spatially locate a region of interest;
    cropping each frame of the video stream to encapsulate the region of interest;
    processing the sequence of frames, by a 3-dimensional convolutional neural network, to determine the spatial and temporal dimensions of each frame of the sequence of frames and to produce a pulse waveform point for each frame of the sequence of frames;
    modifying the temporal dimension of at least one frame with one or more dilations; and
    generating a time series of pulse waveform points to generate the pulse waveform of a subject for the sequence of frames.

2. The computer-implemented method according to claim 1, wherein the video stream includes one or more of a visible-light video stream, a near-infrared video stream, and a thermal video stream of a subject.

3. The computer-implemented method according to claim 2, further comprising:
    combining at least two of the visible-light video stream, the near-infrared video stream, and the thermal video stream into a fused video stream.

4. The computer-implemented method according to claim 3, wherein the visible-light video stream, the near-infrared video stream, and/or the thermal video stream are combined according to a synchronization device.

5. The computer-implemented method according to claim 1, wherein the cropping includes each frame being downsized by bi-cubic interpolation to reduce the number of image pixels.

6. The computer-implemented method according to claim 1, wherein the region of interest includes a face.

7. The computer-implemented method according to claim 1, wherein the region of interest includes two or more body parts.

8. The computer-implemented method according to claim 1, further comprising:
    partitioning the sequence of frames into partially overlapping subsequences,
    wherein a first subsequence of frames overlaps with a second subsequence of frames.

9. The computer-implemented method according to claim 8, further comprising:
    applying a Hann function to each subsequence;
    adding the overlapping subsequences to generate the pulse waveform.

10. The computer-implemented method according to claim 1, further comprising:
    calculating a heart rate or heart rate variability based on the pulse waveform.

11. A system for generating a pulse waveform, the system comprising:
    a processor; and
    a memory storing one or more programs for execution by the processor, the one or more programs including instructions for:
    capturing a video stream including a sequence of frames;
    processing each frame of the video stream to spatially locate a region of interest;
    cropping each frame of the video stream to encapsulate the region of interest;
    processing the sequence of frames, by a 3-dimensional convolutional neural network, to determine the spatial and temporal dimensions of each frame of the sequence of frames and to produce a pulse waveform point for each frame of the sequence of frames;
    modifying the temporal dimension of at least one frame with one or more dilations; and
    generating a time series of pulse waveform points to generate the pulse waveform of a subject for the sequence of frames.

12. The system according to claim 11, wherein the video stream includes one or more of a visible-light video stream, a near-infrared video stream, and a thermal video stream of a subject.

13. The system according to claim 12, further comprising:
    combining at least two of the visible-light video stream, the near-infrared video stream, and the thermal video stream into a fused video stream.

14. The system according to claim 13, wherein the visible-light video stream, the near-infrared video stream, and/or the thermal video stream are combined according to a synchronization device.

15. The system according to claim 11, wherein the cropping includes each frame being downsized by bi-cubic interpolation to reduce the number of image pixels.

16. The system according to claim 11, wherein the region of interest includes a face.

17. The system according to claim 11, wherein the region of interest includes two or more body parts.

18. The system according to claim 11, further comprising:
    partitioning the sequence of frames into partially overlapping subsequences, wherein a first subsequence of frames overlaps with a second subsequence of frames.

19. The system according to claim 18, further comprising:
    applying a Hann function to each subsequence;
    adding the overlapping subsequences to generate the pulse waveform.

20. The system according to claim 11, further comprising:
    calculating a heart rate or heart rate variability based on the pulse waveform.

21. A non-transitory computer-readable medium having instructions stored thereon that, when executed by a processor, cause the processor to generate a pulse waveform, the instructions comprising:
- capturing a video stream including a sequence of frames;
- processing each frame of the video stream to spatially locate a region of interest;
- cropping each frame of the video stream to encapsulate the region of interest;

processing the sequence of frames, by a 3-dimensional convolutional neural network, to determine the spatial and temporal dimensions of each frame of the sequence of frames and to produce a pulse waveform point for each frame of the sequence of frames;
- modifying the temporal dimension of at least one frame with one or more dilations; and
- generating a time series of pulse waveform points to generate the pulse waveform of a subject for the sequence of frames.

* * * * *